(12) United States Patent
Davenport et al.

(10) Patent No.: US 7,899,538 B2
(45) Date of Patent: Mar. 1, 2011

(54) METHODS AND APPARATUS FOR AUTOMATICALLY TRACKING HEART FAILURE STATUS

(75) Inventors: Lynn A. Davenport, Roseville, MN (US); Purvee P. Parikh, San Diego, CA (US); Todd J. Sheldon, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 1009 days.

(21) Appl. No.: 11/691,266

(22) Filed: Mar. 26, 2007

(65) Prior Publication Data
US 2007/0288059 A1    Dec. 13, 2007

Related U.S. Application Data

(60) Provisional application No. 60/745,037, filed on Apr. 18, 2006.

(51) Int. Cl.
*A61N 1/37* (2006.01)
(52) U.S. Cl. ......................................................... 607/37
(58) Field of Classification Search ..................... 607/6, 607/28
See application file for complete search history.

(56) References Cited

U.S. PATENT DOCUMENTS

| | | | | |
|---|---|---|---|---|
| 6,070,101 A | * | 5/2000 | Struble et al. ................... | 607/9 |
| 6,473,647 B1 | * | 10/2002 | Bradley ........................ | 607/27 |
| 6,748,261 B1 | * | 6/2004 | Kroll et al. ................... | 600/510 |
| 7,177,681 B2 | * | 2/2007 | Zhu et al. ........................ | 607/9 |
| 7,632,235 B1 | * | 12/2009 | Karicherla et al. ........... | 600/526 |
| 2003/0023280 A1 | * | 1/2003 | Thompson ...................... | 607/9 |
| 2004/0172080 A1 | | 9/2004 | Stadler et al. | |
| 2005/0215914 A1 | * | 9/2005 | Bornzin et al. .............. | 600/508 |

* cited by examiner

*Primary Examiner*—Carl H Layno
*Assistant Examiner*—Paula J Stice
(74) *Attorney, Agent, or Firm*—Stephen W. Bauer; Reed A. Duthler

(57) ABSTRACT

Assessing symptomatic and asymptomatic physiologic changes due to chronic heart failure involves apparatus and methods for gauging degradation and possible improvement using automated measurement of inter-ventricular conduction time, both alone and in combination with other automated physiologic tests. Conduction times increase due to the greater distance a wavefront must traverse as a heart enlarges. Analysis of conduction time can be used to verify the occurrence of cardiac remodeling due to heart failure as well as beneficial reverse remodeling due to successful heart failure therapy delivery. Patient activity level(s) and presence/increase in pulmonary fluids can also be used to automatically determine changes in heart failure status and/or predict hospitalization. Conduction time is monitored between electrodes positioned in the left and right ventricles of the heart via endocardial or epicardial electrodes.

18 Claims, 11 Drawing Sheets

METHODS AND APPARATUS FOR AUTOMATICALLY TRACKING HEART FAILURE STATUS

CROSS REFERENCE TO RELATED APPLICATIONS

This application claims the benefit of the filing of provisional U.S. patent application Ser. No. 60/745,037 entitled, "INTERVENTRICULAR CONDUCTION TIME RELATED TO SIZE OF HEART," filed 18 Apr. 2006 the contents of which are hereby fully incorporated herein. In addition, this application hereby incorporates the contents of co-pending U.S. patent application Ser. No. 10/727,008 entitled, "METHOD AND APPARATUS FOR DETECTING CHANGE IN INTRATHORACIC ELECTRICAL IMPEDANCE," by Stadler et al. which was filed 3 Dec. 2003 and published 2 Sep. 2004 as publication number US 2004/0172080.

FIELD OF THE INVENTION

The invention relates to cardiac health and, more particularly, to apparatus and methods for gauging changes (improvement and degradation) of heart failure status and cardiac conditions using automated measurement of inter-ventricular conduction time (IVCT) both alone and in combination with other automatically collected physiologic parameters.

SUMMARY

The invention is directed to techniques for monitoring disease-related changes in the myocardial substrate with an emphasis on a more reliable index of the heart failure decompensation (e.g., acute enlargement of the heart) that is based on inter-ventricular conduction time.

In particular, the techniques involve detection and analysis of changes in electrical conduction velocity within the heart to monitor changes in the condition of the heart muscle and thereby indicate possible worsening or improvement of the myocardial substrate. That is, relative changes in the size of the heart can be detected which is known as remodeling when the heart enlarges and reverse remodeling when the heart has reduced overall volume.

For example, assuming relatively constant inter-ventricular conduction time (IVCT) during certain times of the day a periodic assessment of the relative size of a heart failure patient's heart is performed. That is, a current IVCT is compared to one of more prior IVCT and a longer IVCT implies an expanding chamber or chambers of the heart. The IVCT measurements that indicate an enlarged heart condition are stored and/or used to trigger a clinician or patient notification.

Thus, analysis of electrical conduction velocity or, alternatively, conduction time between two fixed electrodes in contact with the heart, can be used to verify the occurrence of heart failure decompensation in a more reliable manner. Accordingly, in the text below, the term "conduction velocity" may broadly refer to representation of electrical propagation as measured by conduction time between two individual fixed electrodes. Alternatively, the conduction time may be measured between two pairs of fixed electrodes (e.g., in a bipolar electrode arrangement).

The conduction time may be monitored between electrodes positioned in or on the left and right ventricles of the heart. The electrodes may be endocardial or epicardial electrodes. In some cases, one of the electrodes may be endocardial and another electrode may be epicardial. In general, the techniques may involve launching a wave front from a first electrode and sensing the arrival of this wave front at a second electrode to assess average conduction time across the heart tissue. More particularly, a stimulus that initiates myocardial depolarization is delivered to the first electrode or pair of electrodes. The second electrode or pair of electrodes then senses the arrival of the wave front as local cardiac depolarization. The time between launching the wave front at the first electrode(s) and sensing the local cardiac depolarization at the second electrode(s) provides an indication of conduction velocity and, hence, the size or dimensions of the heart. Disease-related changes in myocardial substrate, e.g., manifesting in acute dilation of one or more chambers of the heart, can be detected based on changes in this time.

The techniques for analysis of conduction velocity may be implemented within an implantable medical device (IMD). A change in conduction time represents a change in conduction velocity, and may be used as an independent mode for verification of the heart failure decompensation. Alternatively, changes in conduction time may be considered in combination with other diagnostic or monitoring techniques and features, such as intra-cardiac impedance measurements (to detect pulmonary edema) and/or also monitoring the patient's activity via an accelerometer or piezoelectric sensor within the IMD. That is, a further alternative, the conduction time may be considered in combination with a patient activity level, e.g., as indicated by an accelerometer signal, to distinguish changes in conduction time that occur with changes in activity level from those that occur when the heart rapidly enlarges. The change in conduction time may be compared to a threshold values or prior times measured during similar conditions (e.g., same or similar heart rate, activity, posture, and the like) in an effort to make the measurements comparable and less likely to reflect another variable. Along those lines, the time-rate-of-change in conduction time may be analyzed to distinguish changes from anomalous changes that may be caused by other factors.

In one embodiment, the invention provides a method comprising detecting cardiac conduction time, and indicating the relative size of the heart based on the detected conduction time.

In another embodiment, the invention provides a device comprising a detector to detect cardiac conduction time, and indicate heart volume based on the detected conduction time.

In an added embodiment, the invention provides a device comprising means for detecting cardiac conduction time, and means for indicating the relative size of the heart based on the detected conduction time.

In a further embodiment, the invention provides a method comprising launching a first stimulation wave front from a first ventricular chamber, sensing a first local cardiac depolarization in a second ventricular chamber, detecting a first time between launching the first wave front and sensing the first local cardiac depolarization, launching a second stimulation wave front from the second ventricular chamber, sensing a second local cardiac depolarization in the first ventricular chamber, detecting a second time between launching the second wave front and sensing the second local cardiac depolarization, and indicating the relative size of the heart based on the first time and the second time.

In another embodiment, the invention provides a device comprising means for launching a first stimulation wave front from a first ventricular chamber, means for sensing a first local cardiac depolarization in a second ventricular chamber, means for detecting a first time between launching the first wave front and sensing the first local cardiac depolarization, means for launching a second stimulation wave front from the second ventricular chamber, means for sensing a second local cardiac depolarization in the first ventricular chamber, means for detecting a second time between launching the second wave front and sensing the second local cardiac depolarization, and means for indicating the relative size of the heart based on the first time and the second time.

The invention may provide a number of advantages. In accordance with the invention, detection of changes in electrical conduction velocity within the heart, e.g., via measurement of conduction time, may provide a more reliable indication of an improvement or degradation in a patient's heart failure condition. In particular, the invention may be useful in increasing the specificity of acute heart failure decompensation, generally avoiding false indication of worsening heart failure events due to axis shifts, electrical noise, cardiac pacing stimuli, high sinus or tachycardia rates, or other factors that undermine the effectiveness of existing techniques. The invention may also be useful in increasing the sophistication of heart failure therapy delivery by detecting acute changes in heart volume that are not manifested in ECG or EGM waveforms. In addition, in some embodiments, the invention can be useful in quantifying a degree or severity of heart failure according to the amount and/or rate of change in conduction time.

Optionally, an ECG or EGM waveform can be interrogated for S-T segment deviations, which closely correlates to an episode of ischemia and the methods according to the invention can be rescheduled as ischemia also typically slows conduction time. Alternatively, in the event that such a pre-test for ischemia indicates the presence of an ischemic myocardial substrate, a clinician and/or patient notification or alarm can be activated. Subsequent to resolution of such an ischemic episode the methods according to the invention can be performed as described and depicted herein.

The above summary of the invention is not intended to describe every embodiment of the invention. The details of one or more embodiments of the invention are set forth in the accompanying drawings and the description below. Other features, objects, and advantages of the invention will be apparent from the description and drawings, and from the claims.

DETAILED DESCRIPTION

Figure 1:
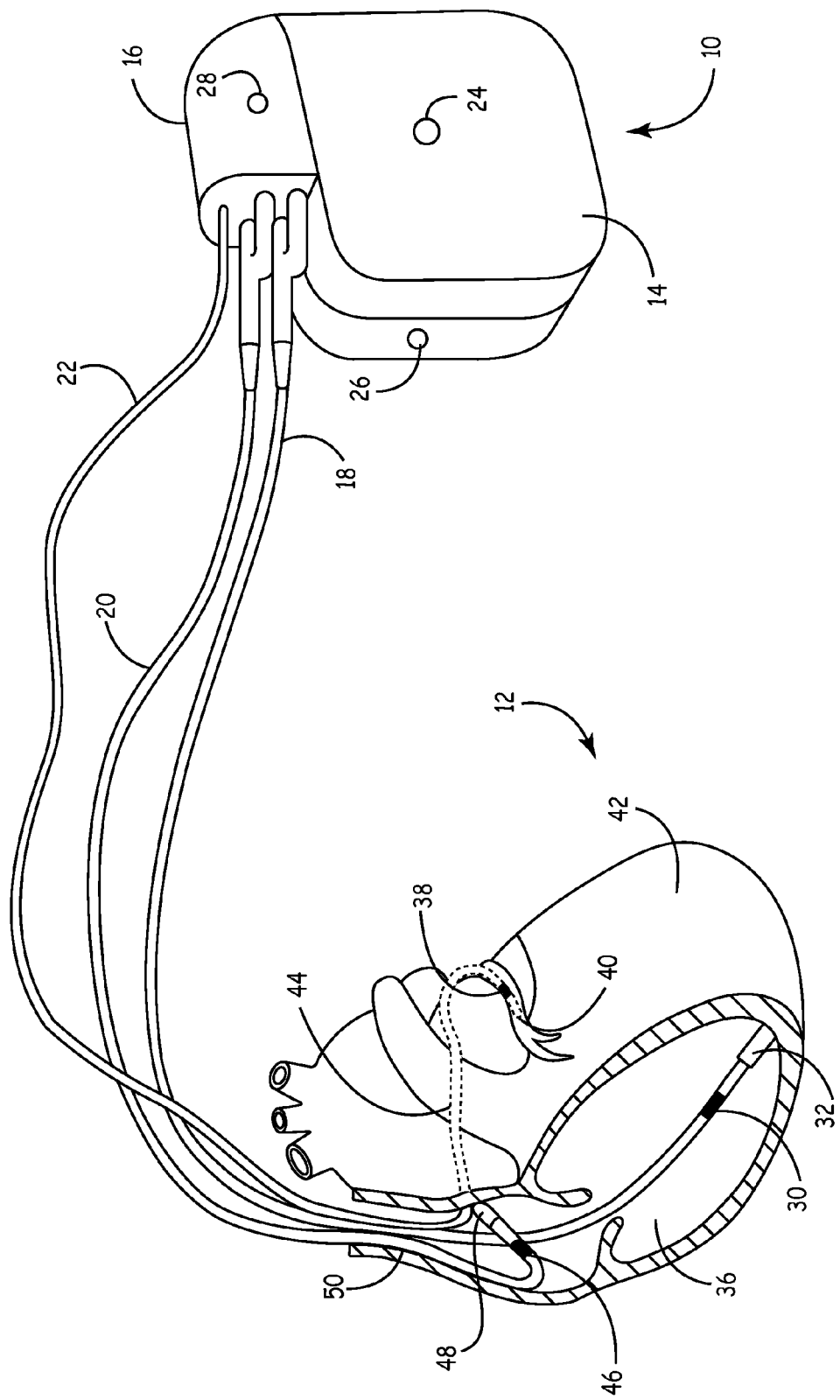
FIG. 1 is a diagram illustrating an exemplary implantable medical device (IMD) in association with a heart.

FIG. 1 is a diagram illustrating an exemplary implantable medical device (IMD) 10 in association with a human heart 12. IMD 10 may be dedicated to monitoring of heart 12, or integrate both monitoring and therapy features, as will be described. In accordance with the invention, IMD 10 is configured to detect cardiac conduction velocity, via measurement of conduction time, and determine whether the volume or size of the heart has changed appreciably based on the detected conduction time. Using conduction time, IMD 10 detects changes in the state of heart 12, and thereby obtains an indication of heart tissue conditions suggestive of heart failure decompensation of the heart 12.

When a change in cardiac conduction time reveals changing dimensions of a heart, IMD 10 initiates at least one of a storage of the measurements and notification to a clinician or patient. Conduction time tends to increase as the heart enlarges. Consequently, changes in the conduction time between two fixed electrodes provide an indication that the overall volume of a heart is changing. In some embodiments, IMD 10 may monitor both conduction time changes and other parameters such as fluid buildup from a baseline and patient activity level to identify and/or confirm that heart failure decompensation is occurring. With regard to fluid buildup (i.e., pulmonary edema), apparatus and methods of monitoring intracardiac impedance can be employed as described, depicted and claimed in U.S. patent application Ser. No. 10/727,008 entitled, "METHOD AND APPARATUS FOR DETECTING CHANGE IN INTRATHORACIC ELECTRICAL IMPEDANCE," filed 3 Dec. 2003 and assigned to Medtronic, Inc. the contents of which are fully incorporated herein.

As shown in FIG. 1, IMD 10 may be generally flat and thin to permit subcutaneous implantation within a human body, e.g., within upper thoracic regions or the lower abdominal region. IMD 10 may include a hermetically sealed housing 14 having a connector block assembly 16 that receives the proximal ends of one or more cardiac leads for connection to circuitry enclosed within the housing. In the example of FIG. 1, connector block assembly 16 receives three cardiac leads. In particular, connector block assembly 16 receives a right ventricular endocardial lead 18, a left ventricular epicardial lead 22, and a right atrial endocardial lead 20. In addition, housing 14 may function as an electrode, along with a set of electrodes 24, 26, 28 provided at various locations on the housing or connector block assembly 16.

Ventricular leads 18, 22 may include, in some embodiments, pacing electrodes and defibrillation coil electrodes (not shown) in the event IMD 10 is configured to provide pacing, cardioversion and defibrillation. In addition, ventricular leads 18, 22 may deliver pacing stimuli in a coordinated fashion to provide biventricular pacing and cardiac resynchronization. Electrodes 24, 26, 28 may form a variety of sensing pairs with electrodes carried by leads 18, 20, 22 to obtain different sets of desired EGM data for heart 12.

To detect cardiac conduction time, in accordance with the invention, right ventricular lead 18 includes a signal transmitting electrode 32 adjacent a distal end of the right ventricular lead within right ventricle 36 of heart 12. Right ventricular lead 18 may carry other sense or stimulation electrodes, such as electrode 30 shown in FIG. 1. In addition, left ventricular lead 22 includes a signal sensing electrode 38 adjacent a distal end 40 of the left ventricular lead. Electrodes 32,38 transmit and sense electrical potentials in relation to a reference electrode, which may be carried on IMD 10, e.g., as part of housing 14. Alternatively, the reference electrode may be provided as part of a bipolar electrode configuration carried by the respective lead 18, 22. Left ventricular lead 22 may be deployed to contact left ventricle 42 via the coronary sinus and coronary vein 44. Atrial lead 20 may be provided to permit atrial sensing, and may include an electrode 46 adjacent a distal end 48 of the right atrial lead within right atrium 50.

In operation IMD 10 drives signal transmitting electrode 32 via right ventricular lead 18 to apply a stimulation wave front to right ventricle 36. The wave front is selected to have an amplitude and pulse width sufficient to initiate myocardial depolarization in right ventricle 36. Sensing electrode 38 senses a localized cardiac depolarization in left ventricle 42 upon propagation of the depolarization wave front from right ventricle 36, and communicates the sensed signal to IMD 10 via left ventricular lead 22. IMD 10 may include sensor circuitry to process the received signal. In addition, IMD 10 may include detector circuitry to determine a conduction time based on the time delay between application of the stimulation wave front in right ventricle 36 and sensing of the local depolarization in left ventricle 42. In this manner, the detection circuitry permits detection of changes in overall volume of the heart based on a change in the detected conduction time.

The cardiac conduction time can vary as a function of the condition of tissue within heart 12, such ischemia, which can itself affect conduction velocity and, therefore IVCT. Thus, optionally, in advance of (or during) performance of the methods of the invention, a test can be performed to see if an ischemic condition is present. If so the methods of the invention can be rescheduled (or canceled) until a later time. In the event that no ischemic condition is present, then upon detection of changes in measured IVCT values, IMD 10 may activate an alarm or provide other notification(s) to the patient and/or clinician(s). Alternatively or in addition to alarm activation, IMD 10 may select a therapy and coordinate the delivery of the therapy by IMD or some other device. In addition, in the event the therapy involves electrical stimulation, the amplitude, frequency, or pulse width of stimulating current can be controlled as necessary to ensure, as applicable, continued pacing capture and/or efficacious defibrillation thresholds (DFTs) for an enlarged myocardial mass. As a further alternative, determination of the severity of change in cardiac condition can be used to choose other types of therapy such as drug delivery, as well as types, dosages and durations of drug delivery as is known and practiced in the delivery of therapy to heart failure patients.

Figure 2:
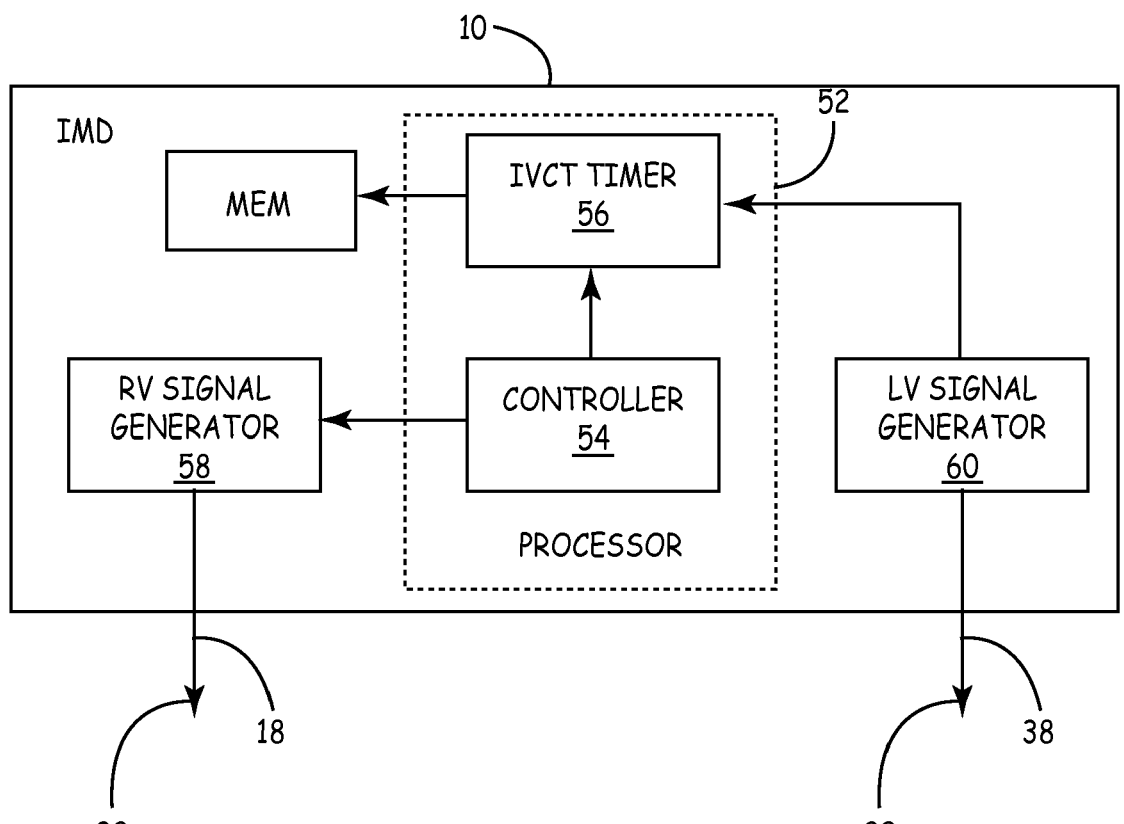
FIG. 2 is a block diagram illustrating a device for determining IVTC and storing the measured values as a surrogate for heart size.

FIG. 2 is a block diagram illustrating an IMD 10 configured for measurement of IVCT based on heart tissue conduction time, in accordance with the invention. As shown in FIG. 2 device 10 may include a processor 52 that controls the application of the stimulation wave front in right ventricle 36 and sensing of a localized depolarization in left ventricle 42 to evaluate cardiac conduction time across tissue between electrodes within the right and left ventricles 36, 42 of heart 12. Processor 52 may be realized by a microprocessor, digital signal processor, ASIC, FPGA, or other integrated or discrete logic circuitry programmed or otherwise configured to provide functionality as described herein.

Processor 52 may function to provide, for example, a controller 54 and an ischemia detector 56. Controller 54 and IVCT timer 56 may be programmable features or functional blocks of processor 52. Controller 54 controls the operation of right ventricular signal generator circuitry 58. Signal generator circuitry 58, in response to a control signal from controller 54, launches a stimulation wave front into right ventricle 36 via signal transmitting electrode 32 of right ventricular lead 18.

For patients with little or no intrinsic rhythm, such as patients with second or third degree AV conduction block, that are paced for a majority or all of the time, the stimulation wave front can be readily coordinated with pacing pulses. In particular, right ventricular pacing pulses may be used as the stimulation wave front that initiates a myocardial depolarization in right ventricle 36, which then propagates across the cardiac tissue to cause a local depolarization in left ventricle 42. In patients with normal sinus activity, overdrive pacing slightly above the sinus rate can be performed at regular intervals to obtain the conduction times. The time interval for measurements can be a programmable parameter of IMD 10, which may be patient specific and set at the discretion of the physician. In one embodiment of the invention measurement of IVCT occurs during relatively similar patient activity, heart rate, and/or in a common posture to help reduce possibly transient or non-comparable measurements.

Left ventricular sensor circuitry 60, coupled to left ventricular lead 22, captures the sensed depolarization received at measurement electrode 38. Sensor circuitry 60 may amplify, condition and digitize the depolarization signal, and provide the signal in digital form to ischemia detector 56. In some embodiments, sensor circuitry 60 may merely present to ischemia detector 56 a timing signal indicative of the arrival of the depolarization at measurement electrode 38 for comparison to the transmission time of the stimulation wave front at transmitting electrode 32.

As an alternative to transmission of the stimulation wave front via right ventricular lead 18 and sensing via left ventricular lead 22, the left ventricular lead could be equipped with a set of bipolar epicardial electrodes. In this case, conduction time can be measured at the surface of the left ventricle 42 by transmitting a stimulation wave front between the bipolar electrodes of left ventricular lead 22. The bipolar electrodes may be disposed at different axial positions along the length of left ventricular lead 22, and may be approximately 1 to 2 cm apart from one another.

An epicardial arrangement may be particularly effective in identifying the onset of ischemia because the effect of ischemia is first felt in the epicardial layers of the cardiac tissue. As a result, changes in conduction time between a pair of epicardial electrodes carried by left ventricular lead 22 may serve to provide an early warning of heart failure decompensation, progression, and/or imminent heart failure hospitalization. Moreover, proximity of a pair of left ventricular epicardial electrodes to the left anterior descending (LAD) and circumflex arteries, the two most commonly occluded arteries, would make such a configuration particularly sensitive to detection of a possibly acutely decompensating heart failure episode.

In operation, IVCT timer 56 tracks the time the stimulation wave front was applied by right ventricular lead 18 and the time the resulting depolarization was sensed by left ventricular lead 22 to determine the conduction time across the heart tissue between right and left ventricles 36, 42 of heart 12. As heart failure progresses and the IVCT progressively increases, it is assumed that the conduction velocity between the two electrodes on leads 18, 22 is essentially constant (thus the pre-test for possible ischemic conditions).

Heart failure progression (e.g., enlargement of the heart) can be detected when the conduction time is longer than a threshold value. The threshold value may be a nominal value derived from a typical implanted cardioverter-defibrillator device (ICD) population of patients. Alternatively, the threshold value may be independently adjusted and set for a given patient as desired by the attending physician. For diagnosis purposes, the more recent values of the conduction time, e.g., with a time and date stamp, as well as other information, may be stored in a memory associated with IMD 10 along with the most recent arrhythmia to facilitate diagnosis of any association between the onset of ischemia and arrhythmia episodes.

Over a period of time, processor 52 may collect a series of conduction time samples as a function of the measured conduction time. With each sample, IVCT timer 56 compares the conduction time to a baseline conduction time evaluated in one or more previous samples to identify a change in conduction time. The baseline conduction time may be updated over time. For example, the baseline conduction time may represent a mean or median conduction time over a period of n preceding samples.

When the change in conduction time exceeds a predetermined threshold a notification and/or alarm signal can be generated, stored, and/or telemetered to a remote display device (not shown). The change in conduction time may be measured based on a single sample, or based on the mean or median conduction time change over a series of samples. The alarm or notification signal may be used to drive selection and delivery of one or more therapies (manually or automatically—for instance via a drug pump).

Figure 3:
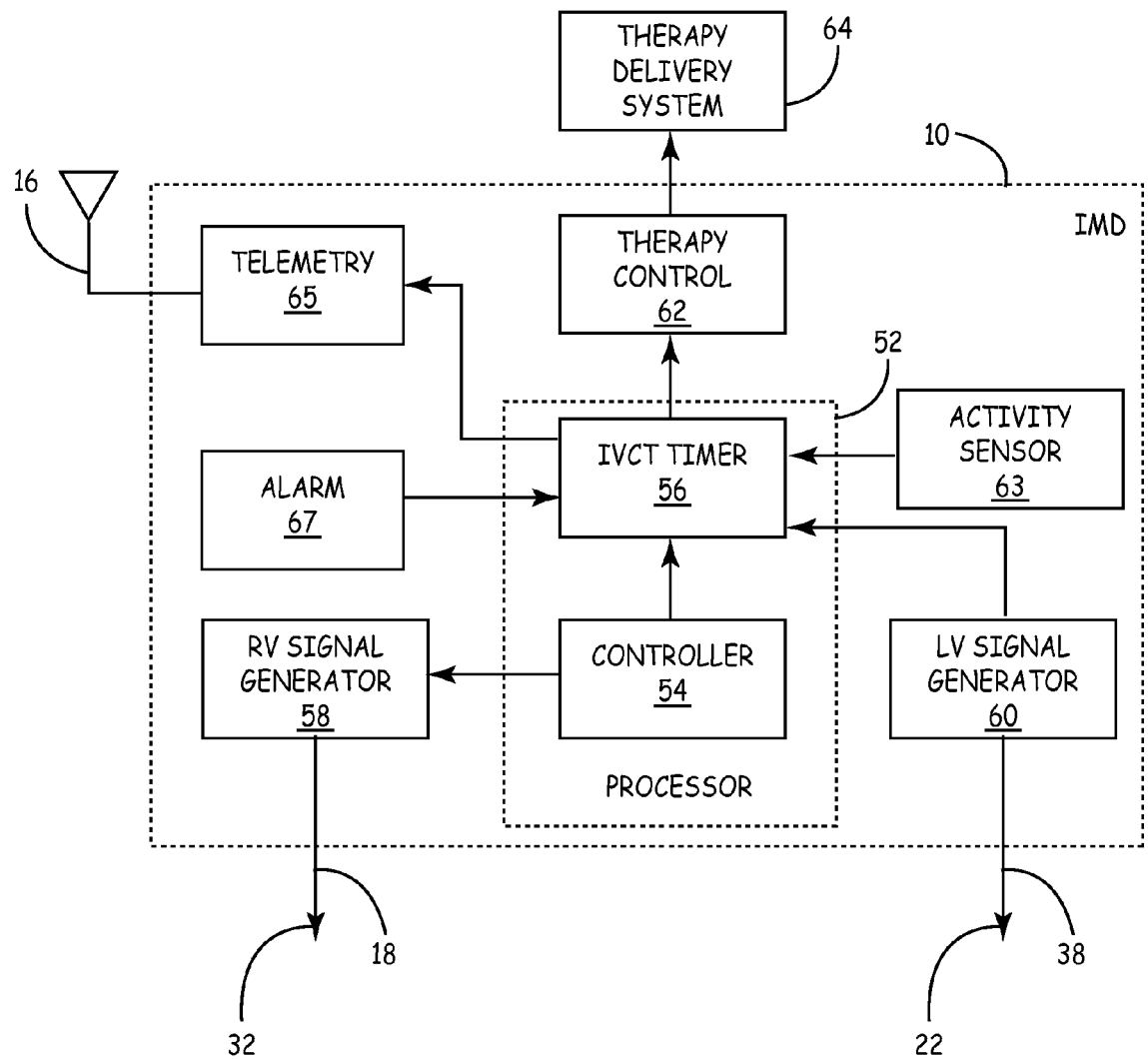
FIG. 3 is a block diagram illustrating a device for determining patient activity and IVTC and storing the measured values as a surrogate for heart size (and heart failure status) and providing a signal (e.g., an alarm of clinician notification) related to the determination via telemetry and/or providing a palliative therapy.

FIG. 3 is a block diagram illustrating an IMD 10' configured for detection of heart failure status or cardiac condition and delivery of therapy. IMD 10' of FIG. 3 corresponds substantially to IMD 10 of FIG. 2, but further includes both a therapy control circuit 62 that drives a therapy delivery system 64, and a telemetry circuitry 65 that drives an antenna 66. IMD 10 also may include an activity level sensor 63 to indicate a level of physical activity of a patient in which the IMD is implanted. Activity level sensor 63 may include, for example, an accelerometer. When the IMD detects a change in conduction time that exceeds a threshold, it transmits a signal to therapy control circuitry 62, which may interact with a therapy delivery system 64 within IMD 10' or associated with another device, or both.

Therapy delivery system 64 may take the form of a drug delivery system or electrical stimulation system such as a neurostimulation, pacing, cardioversion or defibrillation circuit. For example, in some embodiments, therapy control circuitry 62 may interact with an electrical stimulation therapy device integrated with IMD 10' to deliver pacing, post-extrasystolic potentiation, cardioversion or defibrillation therapy, and also communicate with a drug delivery device that may be implanted or external to deliver drug therapy to the patient. In addition, telemetry circuitry 65 may alert an external monitoring system by wireless communication via antenna 66. IMD 10' also may include internal alarm circuitry 67 that is responsive to the signal produced by the IVCT measurement unit 56.

In addition, as mentioned previously, some embodiments of the invention include a pre-test for ischemia. Thus, IMD 10' may include electrocardiogram signal analysis circuitry for identifying deviation of the ST segment of the electrocardiogram as an indication of ischemia. In this manner, IMD 10' can utilize analysis of both conduction time and ST segment deviation to detect ischemia. If IMD 10' detects an ST segment deviation greater than a given ST threshold, for example, in combination with a conduction time change that exceeds another threshold, IMD 10' may identify an ischemic episode. In this manner, the conduction time change can provide confirmation that the ST segment deviation is due to an ischemic condition, rather than an anomalous ST segment deviation caused by factors other than ischemia. Alternatively, the sensitivity to ischemia could be increased by identifying an ischemic episode when either the conduction time or an ST-segment deviation are detected. Once the ischemia condition resolves performance of the remaining steps of the inventive method can proceed.

Based on the amount of conduction time change, IMD 10 also may quantify the severity of the changes in cardiac condition. In some embodiments, the signal transmitted by IVCT measurement unit 60 may specify selection of a particular type of therapy, e.g., drug delivery and/or electrical stimulation, as well as the level, dosage, amplitude, and duration of the therapy, based on the indications of the severity of the changing cardiac condition determined from the amount of conduction time change.

Telemetry circuitry 65, as discussed above, communicates an indication of the cardiac condition to an external device via antenna 66. Thus, the indication may be a wireless, radio frequency message that indicates simply the presence of a possible degradation (or improvement) in heart failure condition and, in some embodiments, the severity of the condition. In addition, IMD 10' itself may have an audible alarm within alarm circuitry 67 that notifies the patient when an episode of heart failure progression (i.e., degradation) or improvement is occurring. The external device that receives the wireless message may be a programmer/output device that advises a physician or other attendant of the conditions (e.g., via a display or a visible or audible alarm). Also, the recorded measurements and events may be stored in memory in the external device, or within the IMD 10', for review by a physician.

The components of IMD 10, with the exception of leads 18, 22, may be housed in a common housing such as that shown in FIG. 1. Alternatively, portions of IMD 10' may be housed separately. For example, therapy delivery system 64 could be integrated with IMD 10' or provided in a separate housing, particularly where the therapy delivery system includes drug delivery capabilities. In this case, therapy control circuit 62 may interact with therapy delivery system 64 via an electrical cable or wireless link.

Figure 4:
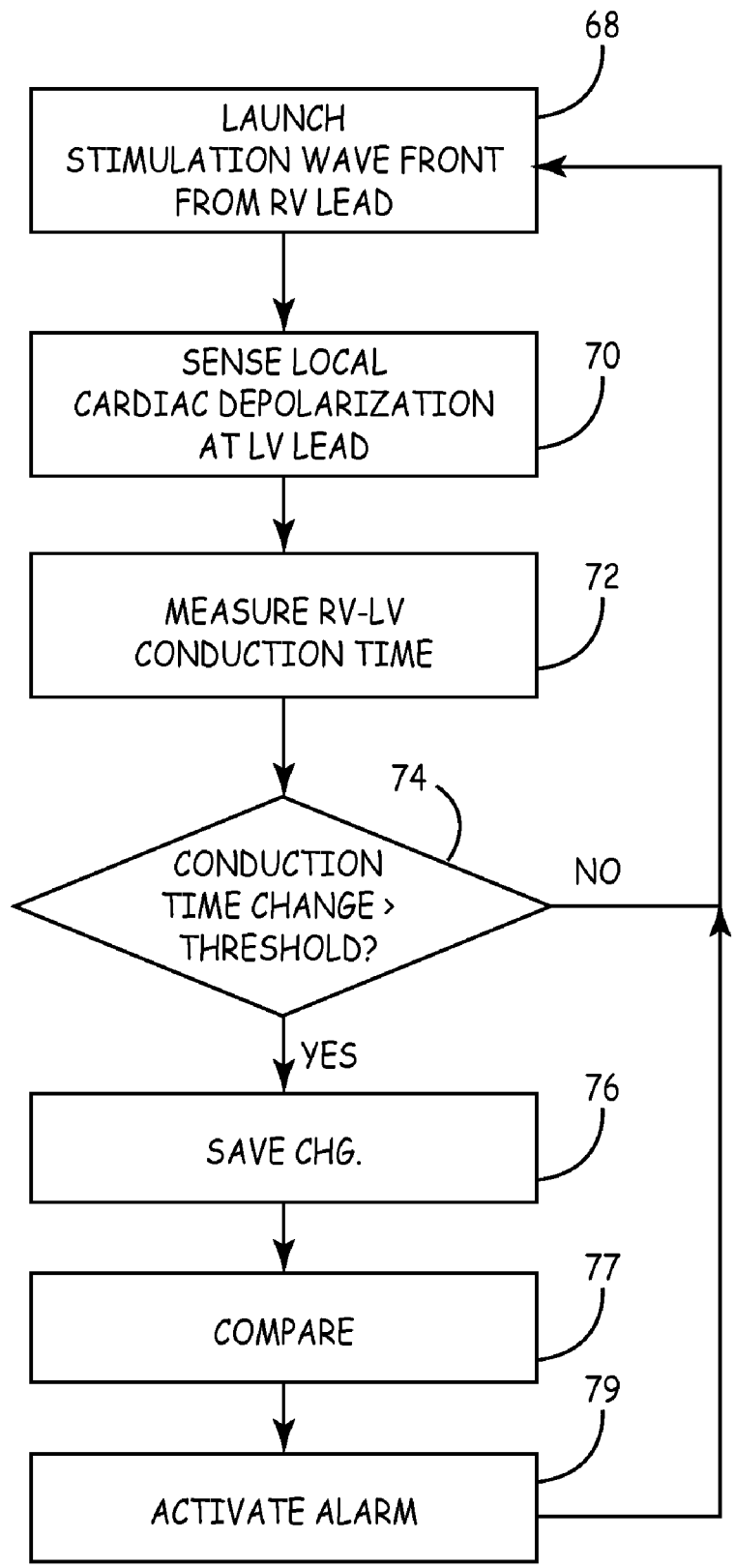
FIG. 4 is a flow diagram illustrating a technique for determining IVTC and storing the measured values as a surrogate for heart size, comparing changes in conduction time, and activating an alarm (or other notification to a patient or clinician) in the event that the comparison reveals a supra-threshold change in conduction time.

FIG. 4 is a flow diagram illustrating a technique for detection of changing heart condition based on conduction time. In general, the process may include launching a stimulation wave front from the right ventricular lead 18 (68), detecting a local cardiac depolarization at the left ventricular lead 22 (70), and measuring the conduction time between the right and left ventricular leads 18, 22 (72). The conduction time may be determined based on the time required for the depolarization initiated by the stimulation wave front to propagate across the heart tissue from right ventricular lead 18 to left ventricular lead 22 and cause a depolarization in left ventricle 42.

In the example of FIG. 4, the stimulation wave front is transmitted from the right ventricular endocardial lead 18, with the resulting depolarization being sensed by the left ventricular epicardial lead 22. However, an opposite arrangement may be used in which the stimulation wave front is transmitted from the left ventricular epicardial lead 22, and the resulting depolarization is sensed by the right ventricular endocardial lead 18. Moreover, in some embodiments, both leads may be endocardial leads, or both leads may be epicardial leads.

The process involves determining conduction time and then comparing the conduction time to a threshold conduction time (74). More specifically, in certain embodiments, the process compares a change in the conduction time to a change threshold. Again, the change in conduction time may be determined by comparing a mean or median conduction time over a series of samples to a mean or median conduction time for a preceding series of samples. If the change in conduction time exceeds the threshold (74), the process indicates possible changing heart failure condition (76). In some embodiments, the comparison of the conduction time to a threshold may be accompanied by analysis of patient activity and/or intrathoracic fluid status or other parameters that may also help confirm that the heart failure status (or cardiac condition) is changing for the worse (or for the better). Upon detection of such an episode, the process further may involve delivery of therapy (77) and activation of an alarm (79) or other notification.

Figure 5:
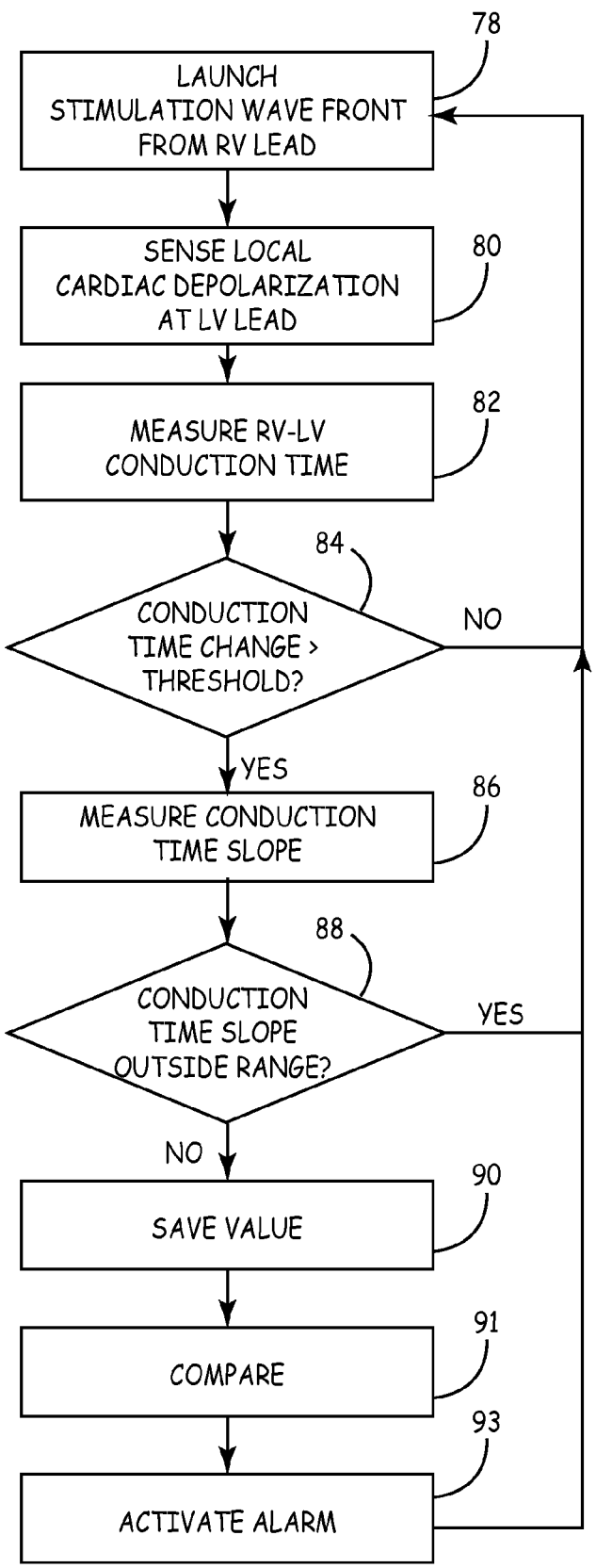
FIG. 5 is a flow diagram illustrating a technique for determining the slope of measured IVTC values, comparing the slope to a desired range (or discrete) values, saving the out-of-range values, comparing them, and activating an alarm (or performing other notification) regarding a patient's relative heart size.

FIG. 5 is a flow diagram illustrating another process for detection of changing heart failure status or cardiac condition based on conduction time. In the example of FIG. 5, the process involves launching a stimulation wave front from the right ventricular lead 18 (78), detecting the resulting depolarization at the left ventricular lead 22 (80), and measuring the conduction time between the right and left ventricular leads 18, 22 (82). Again, the stimulation wave front alternatively may be transmitted from the left ventricular lead 22, with the depolarization sensed at the right ventricular lead 18, and the process is subject to variation in the endocardial or epicardial arrangement of the leads. The process next determines whether the conduction time change is greater than a given threshold (84). In the example of FIG. 5, the process may rely on a static threshold that does not take into account the conduction time associated with previous samples.

If the conduction time change is greater than an applicable threshold (84), the process next measures the slope of the conduction time change (86). The slope of the conduction time change over time can serve to distinguish changes that are indicative of ischemia from spurious changes that may arise due to other factors. For example, many arguable unrelated conditions such as drug therapy, myocardial ischemia, changes in electrolyte concentrations, temperature changes, progression of disease, and the like may influence myocardial conduction time very slowly. Conversely, fusion of stimulated and intrinsic depolarization wave fronts, conduction aberrancy, electrode motion or dislodgement, and the like may influence the measured conduction time very rapidly. For these reasons, the rate of change (i.e., slope) of the conduction time over time may serve to distinguish among various factors influencing conduction time.

Another aspect of the invention involves a probable conclusion that a lead has become dislodged or has materially migrated based upon too large a change in IVCT to qualify as truly physiologic. According to this aspect of the invention is the IVCT changes by, for example, 20% within a day, it is very probably due to a non-physiologic event. In this case, the alarm of notification can convey to a clinician and/or patient that inspection and/or recalibration of the IMD and medical electrical lead system should be undertaken. In addition, the "current IVCT measurement" and "previously recorded IVCT" should be discarded and perhaps any threshold comparison values reprogrammed consistent with the status (e.g., separation) of the IMD/lead system. To improve the specificity of the conclusions drawn based on conduction time according to the invention, the process may be configured to exclude measurements such as those taken during or following dislodgement or material migration of the medical electrical lead(s). Thus, if the conduction time slope falls outside of a desired range (88), i.e., the rate of change is too slow or too fast, the process ignores the conduction time change and does not indicate a physiologic episode. If the conduction time slope is within the desired range, however, the process indicates a valid result (90). In this case, IMD 10 may direct delivery of therapy (91) and activation of an alarm (93).

Again referring to the possibility that ischemic conditions are present, it is known that an increase in conduction time (caused by ischemia) will tend to follow a known time course, typically resulting in a fifty percent (50%) increase in conduction time over a period of one to ten minutes. An increase in conduction time that occurs faster than such a rate generally is not caused by ischemia. Rather, the likely cause of the increase in conduction time will be a conduction aberrancy, electrode motion or dislodgement, or conduction block in a section of the myocardium that is refractory. To avoid the possibility of encountering refractive myocardium, it may be desirable to avoid transmission of the stimulation wave front prematurely or immediately following a premature ventricular contraction.

An increase in conduction time that occurs over a time period longer than approximately ten minutes also generally can be attributed to progression of heart failure, in general, and/or enlargement of the overall volume of the heart.

To exclude slow, drifting changes in conduction time, a baseline conduction time, i.e., a normal expected conduction time, may be allowed to change slowly over time. A baseline conduction time may be established over a series of conduction time measurement samples. To exclude fast, sudden changes in conduction time, an adaptive expected range of conduction times can be established. The expected range could be composed, for example, of an adaptive mean of conduction time +/− an adaptive estimate of the variability of conduction times. Measurements of conduction time that occur outside of the expected range may be excluded as outliers. If consecutive measurements are consistently excluded as outliers, a new expected range of conduction times, based on this new steady state value, can be established.

Figure 6:
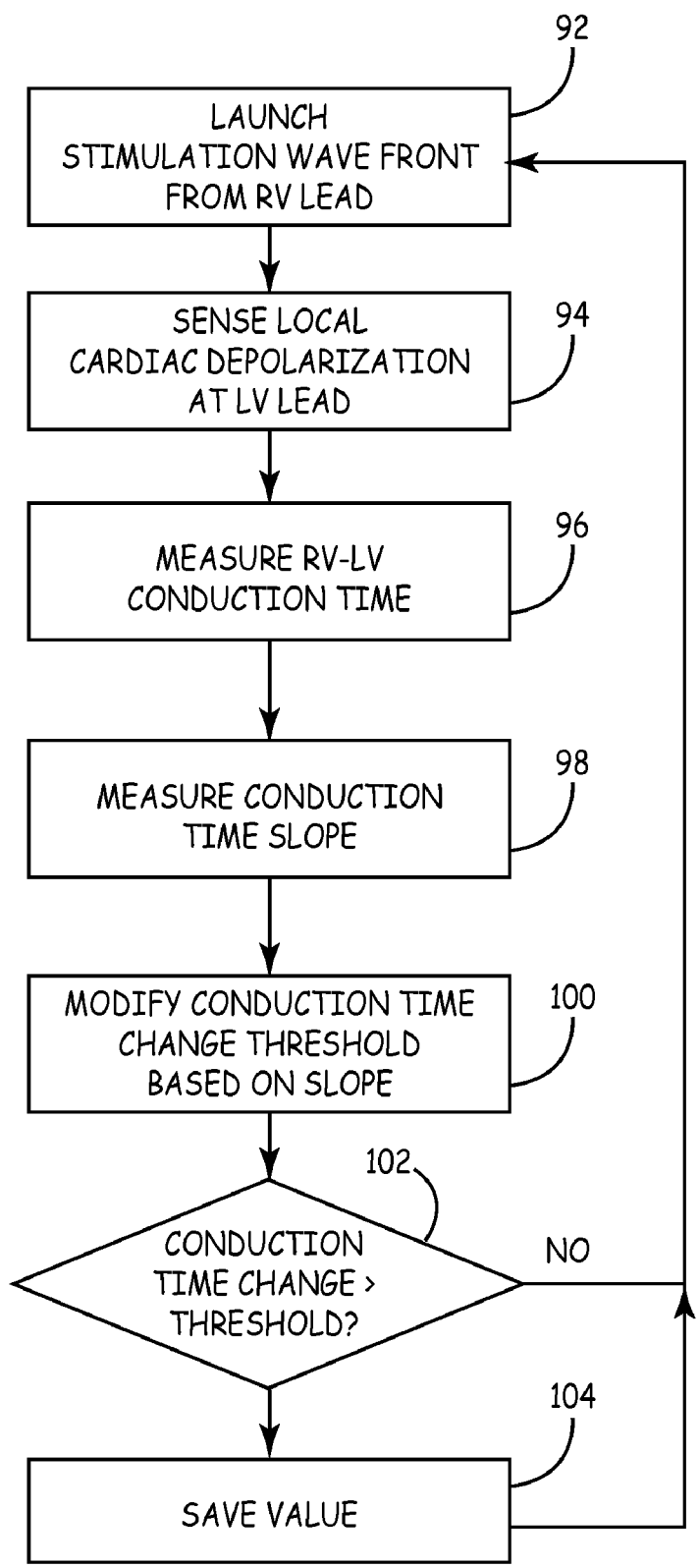
FIG. 6 is a flow diagram illustrating a technique for determining the slope of measured IVTC values, modifying the conduction time change threshold based on the slope of the measured values, comparing the modified threshold to the to a threshold, and saving the measured values.

FIG. 6 is a flow diagram illustrating a further process for detection of changing cardiac condition based on conduction time. The process illustrated in FIG. 6 may correspond substantially to the process of FIG. 5. Instead of using a static conduction time change threshold, however, the process makes use of a dynamic conduction time change threshold that varies as a function of recent conduction time samples. Accordingly, as shown in FIG. 6, the process involves launching a stimulation wave front from the right ventricular lead 18 (92), detecting arrival of the resulting depolarization at the left ventricular lead 22 (94), and measuring the conduction time between the right and left ventricular leads 18, 22 (96).

The process next determines a slope of the conduction time over a series of recent conduction time samples (98). Based on the slope, the process modifies the threshold value of conduction time change (100). In this manner, the process adapts the threshold value for conduction time change to the rate of change in the measured conduction time. If the measured conduction time changes more rapidly, the process may involve increasing the threshold level of the conduction time change before declaring a changing cardiac condition. If the conduction time changes more slowly, the process may involve decreasing the threshold level of the conduction time change before declaring a changing cardiac condition.

The dynamic threshold serves to adapt the process to changing conditions in the conduction time, and can help to avoid declaring a progression in heart failure condition or an improvement in cardiac condition based on momentary, spurious shifts in conduction time. For example, if the conduction time changes abruptly, the level of the conduction time threshold may be increased to require a larger change. If the conduction time change exceeds the threshold (102), the process detects or declares detection of changing cardiac condition (104). In response, IMD 10 may direct delivery of therapy and activation of an alarm (such as alarm 67 in FIG. 3).

Figure 7:
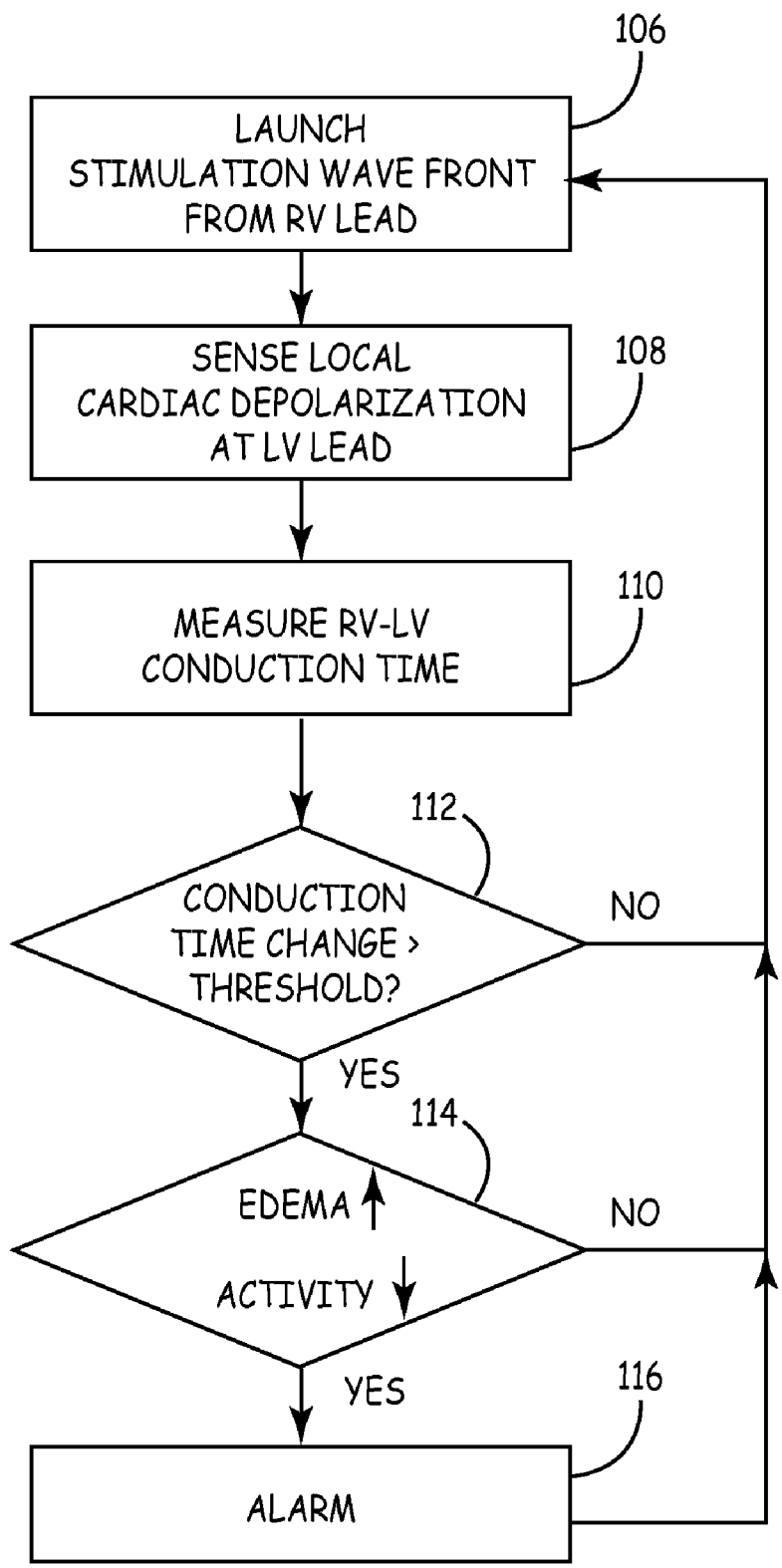
FIG. 7 is a flow diagram illustrating a technique for measuring IVTC values, comparing the values to a threshold, determining whether the patient's activity level is low or decreased and/or determining whether a measured intra-thoracic fluid condition indicative of pulmonary edema is present and if positive determinations are made, and activating an alarm (or performing other notification) regarding a patient's relative heart size and/or possibly worsening heart failure status (e.g., possible imminent heart failure hospitalization for the patient).

FIG. 7 is a flow diagram illustrating a process for determining whether cardiac condition or heart failure status is changing based on conduction time, increase intrathoracic fluid load (e.g., pulmonary edema), and decrease or low level of patient activity. As shown in FIG. 7, the process involves launching a wave front from the right ventricular lead 18 (106), detecting the conducted wave front at the left ventricular lead 22 (108), and measuring the conduction time between the right and left ventricular leads 18, 22 (110). If the conduction time change exceeds an applicable threshold (112), the process analyzes patient activity and/or intrathoracic fluid status to thereby corroborate the determination based wholly upon conduction time. Accordingly, if patient activity is low (or is materially reduced or decreasing over a relatively short period of time) on an actual, current basis or on an time-weighted, average, or mean basis and the intrathoracic fluid load is greater than a recent threshold (or is trending upward), the process indicates positive determination of negatively changing cardiac conditions and/or worsening of heart failure status (116). This may result in delivery of therapy and activation of an alarm system or other notification. In some embodiments, the process of FIG. 7 may be modified such that changing heart failure status is declared when the conduction time change exceeds an applicable threshold and either patient activity is low or decreasing steadily or intrathoracic fluid buildup is occurring. In this manner, the changing conditions are indicated in response to either pair of criterion such that the detection process is less selective but more inclusive, and therefore less likely to miss a positive detection.

Of course, while not specifically depicted herein, in the event that conduction time is decreasing, patient activity is relatively high or trending upward, and intrathoracic fluid status is decreasing or relatively steady over time an improvement in cardiac conditions can be declared. In this event the notifications can include statements or signals to that effect and the patient's drug regime specific to heart failure condition can perhaps we adjusted. This effect is known as reverse remodeling which can result from successful therapy and/or patient compliance and the like.

Figure 8:
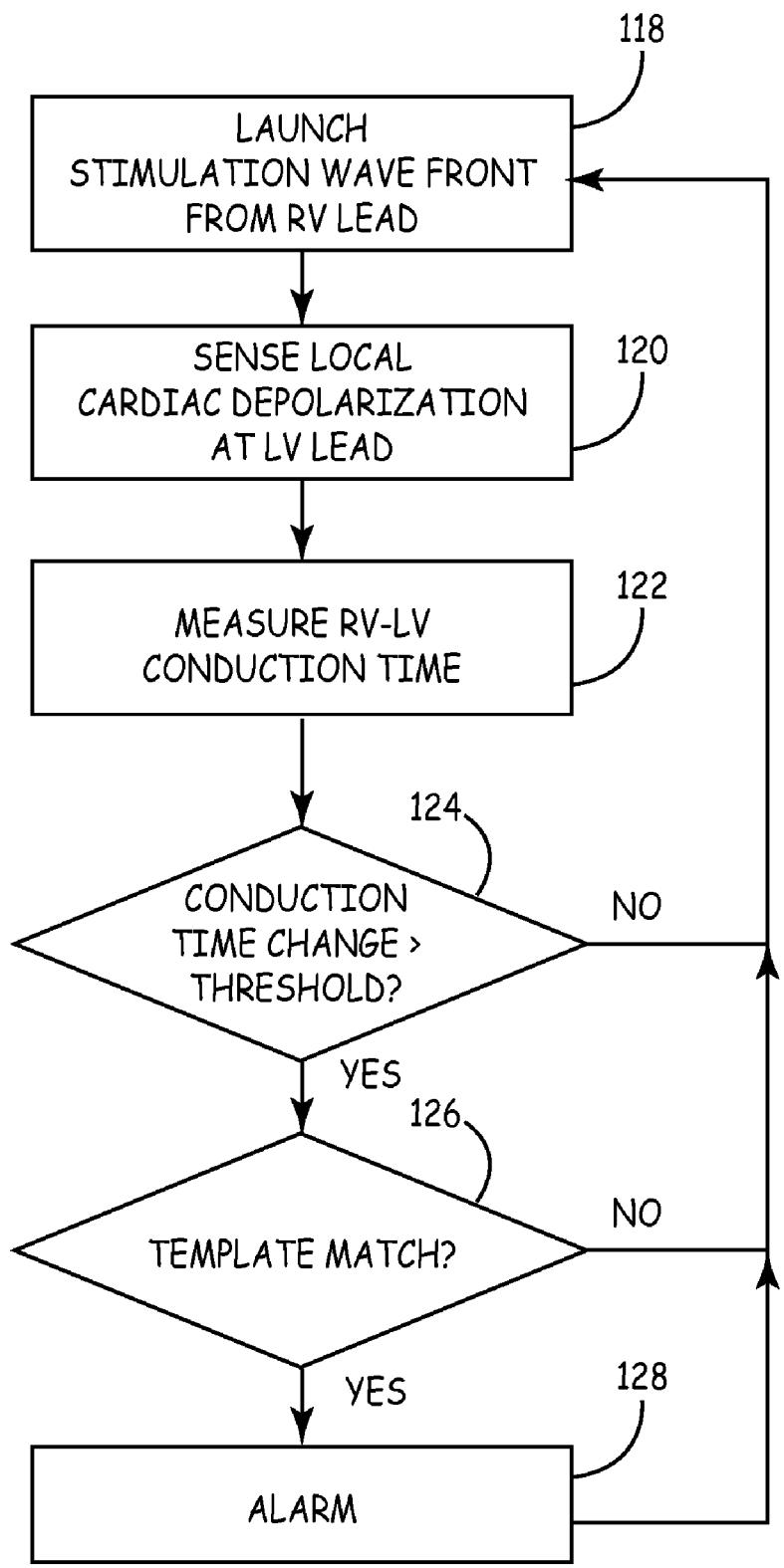
FIG. 8 is a flow diagram illustrating a process for determining IVCT, comparing it to a threshold and if a supra-threshold IVCT is present, comparing it to a template indicative of heart failure decompensation (e.g., via a morphological comparison) or other heart failure-related condition and, in the event that the templates "match" then activating an alarm (or performing other notification) regarding a patient's relative heart size and/or apparently changing heart failure status.

FIG. 8 is a flow diagram illustrating a process for detection of changing heart failure based on conduction time and waveform morphology. The process of FIG. 8 conforms substantially to the process of FIG. 7. For example, the process of FIG. 8 involves launching a stimulation wave front from the right ventricular lead 18 (118), detecting a resulting depolarization at the left ventricular lead 22 (120), and measuring the conduction time between the right and left ventricular leads 18, 22 (122).

If the conduction time change exceeds an applicable threshold (124), the process further evaluates the morphology of the measured signal waveform, i.e., the sensed depolarization wave form, as an alternative or in addition to other analysis. In particular, processor 52 in IMD 10 may be equipped to perform wavelet analysis of other waveform analysis techniques to analyze the morphology of the depolarization signal or other cardiac waveforms within heart 12. If the morphology matches a template corresponding to a normal morphology (126), the process does not declare changing cardiac condition. If the morphology does not match the template (126), i.e., differs significantly from the template, and the conduction time change exceeds the threshold (124), the process indicates changing cardiac condition (128).

In this example, analysis of waveform morphology for the depolarization signal received at left ventricular lead 22 serves to corroborate the changing condition indicated by the change in conduction time. When the heart enlarges a broadening of the detected waveform can be expected. Accordingly, tools such as wavelet analysis may be useful in matching the detected activity against a normal template. A deviation from the template that exceeds a programmed threshold, e.g., waveform width, amplitude, energy, or the like, can be use to signal changing cardiac condition.

Figure 9:
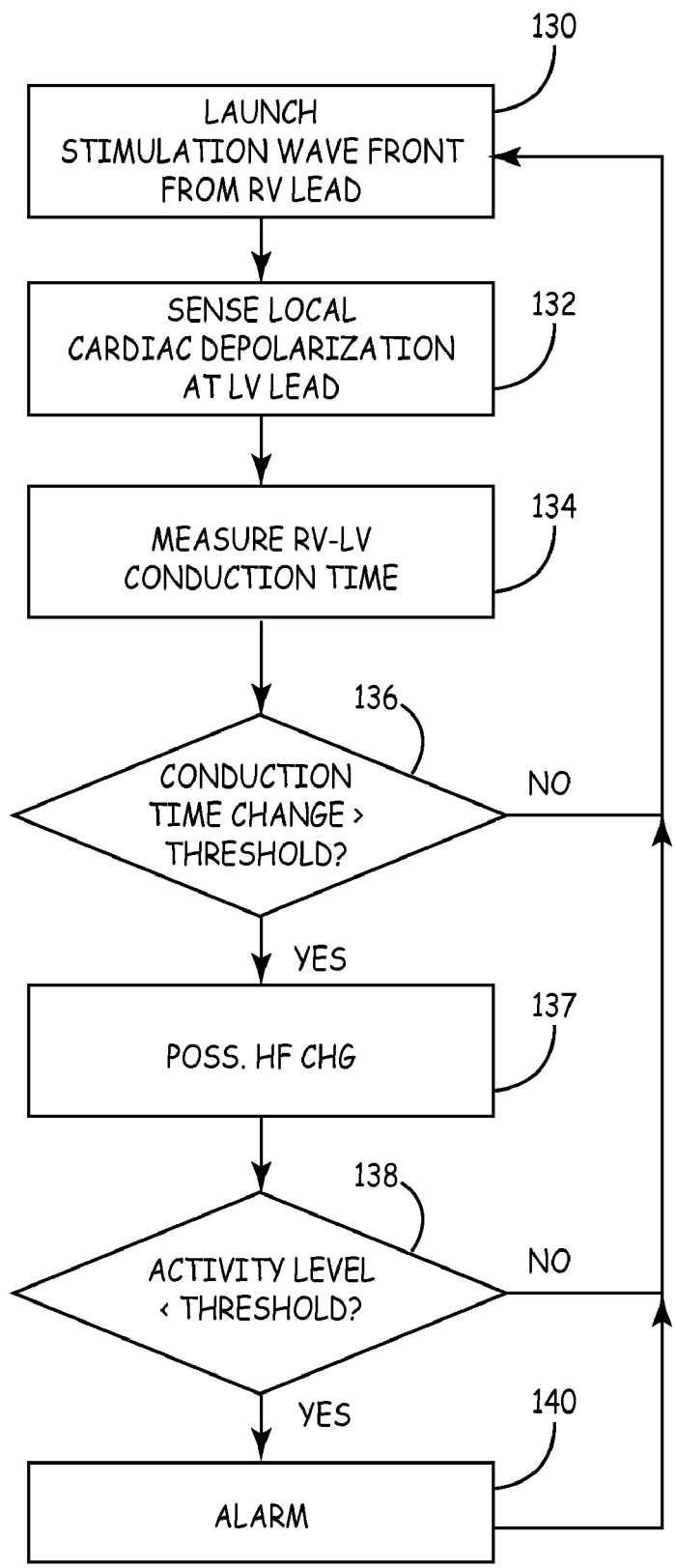
FIG. 9 is a flow diagram illustrating a process for determining IVCT, comparing it to a threshold and if a supra-threshold IVCT is present, comparing it to a template indicative of possible heart failure change (e.g., reverse remodeling or decompensation event or other heart failure-related condition, checking to see if the patient's activity level (present, recent, trend, etc.) is lower than a programmable threshold and in the event that the conduction time exceeds the threshold and the activity level is sub-threshold, then activating an alarm (or performing other notification) regarding a patient's relative heart size and/or apparently changing heart failure status.

FIG. 9 is a flow diagram illustrating a process for detection of changing cardiac condition based on conduction time and activity level. As shown in FIG. 9, the process involves launching a stimulation wave front from the right ventricular lead 18 (130), detecting a resulting depolarization at the left ventricular lead 22 (132), and measuring the conduction time between the right and left ventricular leads 18, 22 (134). If the conduction time change exceeds an applicable threshold (136), the process further involves obtaining an activity level (137), e.g., from an activity level sensor 63 (FIG. 3). The activity level can help to distinguish changes in conduction time that occur with changes in activity level from those changes in conduction time that occur during a heart failure decompensation episode. Accordingly, if the activity level is less than or equal to a threshold (138), and the conduction time is increasing or relatively longer that historically catalogued the process indicates changing cardiac condition (140). If, however, the activity level is greater than the threshold and conduction time is growing shorter or steady, then no determination or declaration of changing cardiac condition is indicated.

Figure 10:
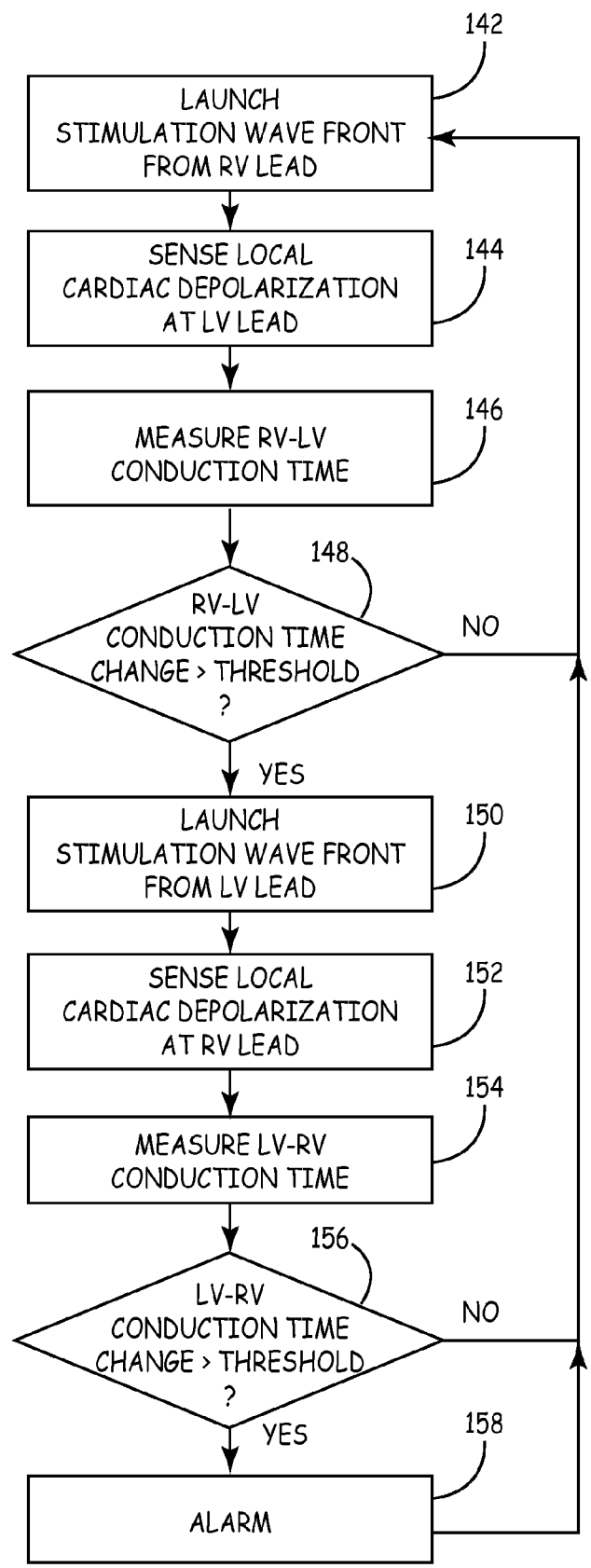
FIG. 10 is a flow diagram illustrating a process for determining IVCT from each direction in an attempt to gauge the overall size of a heart and whether it appears to be enlarged or of less volume than prior measurements (i.e., cardiac conduction time measured from a right ventricle to a left ventricle and cardiac conduction time measured from a left ventricle to a right ventricle) and activating an alarm (or performing other notification) regarding a patient's relative heart size and/or apparently changing heart failure status.

FIG. 10 is a flow diagram illustrating a process for detection of changing heart condition based on both conduction time between the right ventricle and left ventricle (RV-LV) and conduction time between the left ventricle and the right ventricle (LV-RV). As shown in FIG. 10, the process involves launching a stimulation wave front from the right ventricular lead 18 (142), detecting a resulting depolarization at the left ventricular lead 22 (144), and measuring the conduction time between the right and left ventricular leads 18, 22 (146). If the RV-LV conduction time change exceeds an applicable threshold (148), the process further involves launching a stimulation wave front from the left ventricular lead 22 (150), detecting a resulting depolarization at the right ventricular lead 18 (152), and measuring the conduction time between the left and right ventricular leads 22, 18 (154). If the LV-RV conduction time change also exceeds an applicable threshold (156), the process indicates changing heart condition and/or enlargement of the heart (158).

Figure 11:
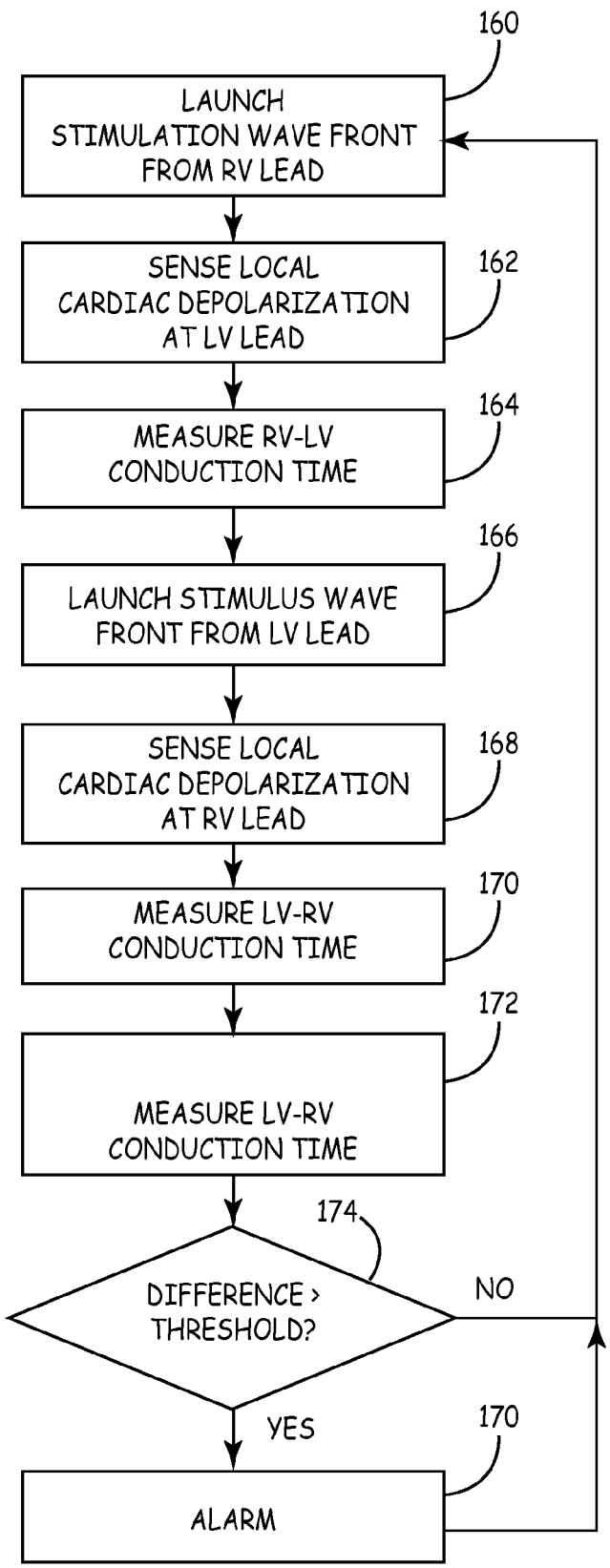
FIG. 11 is a flow diagram illustrating a process for determining a difference in IVCT measured from a right ventricle to a left ventricle and cardiac conduction time measured from a left ventricle to a right ventricle and if the difference exceeds a threshold or has increased appreciably from prior reading(s) and activating an alarm (or performing other notification) regarding a patient's relative heart size and/or apparently changing heart failure status.

FIG. 11 is a flow diagram illustrating a process for detection of changing cardiac condition based on a difference between conduction time between the right ventricle and left ventricle and conduction time between the left ventricle and the right ventricle. As shown in FIG. 11, the process involves launching a stimulation wave front from the right ventricular lead 18 (160), detecting a resulting depolarization at the left ventricular lead 22 (162), and measuring the conduction time between the right and left ventricular leads 18, 22 (164). The process further involves launching a stimulation wave front from the left ventricular lead 22 (166), detecting a resulting depolarization at the right ventricular lead 18 (168), and measuring the conduction time between the left and right ventricular leads 22, 18 (170). Upon computing the difference between the LV-RV conduction time and the LV-RV conduction time (172), the process determines whether the difference is greater than a predetermined threshold (174). A significant difference may be an indication of changing cardiac condition that has increased the distance between the electrodes coupled to the myocardium. Accordingly, if the difference is greater than the predetermined threshold, enlargement of the heart is indicated (176).

Additional variations to the embodiments of the invention described herein are also conceivable. For example, as mentioned previously, the stimulation wave front used to measure conduction time may be launched between a variety of lead arrangements, including right endocardial to left endocardial, left endocardial to right endocardial, right endocardial to left epicardial, left epicardial to right endocardial, right epicardial to left epicardial, left epicardial to right epicardial, left bipolar epicardial, and the like.

In addition, the stimulation wave front may be transmitted as part of a pacing pulse or other therapy pulses or as a dedicated measurement pulse. The stimulation wave front may be transmitted alternatively from the right to the left lead or from the left to the right lead on successive measurement cycles during a single monitoring session to improve sensitivity and specificity for the detection.

As further variations, multiple bipolar electrodes on a single lead may be provided and selected for use in the measurement of conduction time depending on the particular patient's condition. In particular, the measurements (e.g., morphology, rate of change, etc.) captured during a previous heart failure decompensation event can also be used to help confirm that the current measurements are indicative of deleterious progression of heart failure status.

In patients with bi-ventricular pacing, suspension of right ventricular pacing while performing left ventricular pacing could be used to measure conduction time. If appropriate, pacing from the right ventricle and measurement of the depolarization in the left ventricle can be used in some patient populations. In practicing the invention, the blanking interval for the chambers being measured should be reduced (e.g., from a nominal value such as 110 ms to 50 ms) so that the conduction time event can be recorded by the electrodes, amplifiers and related circuitry.

Further, if the patent has a good sinus rhythm, overdrive pacing from one of the locations for a small number of beats may be desirable so that atrial activity and fusion beats do not confound the conduction time measurements. In patients with regular rhythm, one way to prevent incoming atrial activity from undermining the conduction time measurement may be to perform vagal stimulation, if available, or use other means to temporarily prevent AV conduction.

In many cases, the best location for the right ventricular lead may be determined experimentally, e.g., by performing acute occlusion of an artery that seems most likely to suffer from plaque rupture. In some patients, the right ventricular septal location may be the optimum location for conduction time measurement.

As is known and used in the art of IMDs, the methods of the present invention can be encoded in a computer-readable medium and performed under processor control. A "computer-readable medium" includes but is not limited to any particular type of computer memory inasmuch as the medium is capable of generating control signals for operating the components of the IMD. Without limitation this includes conventional memory, floppy disks, EEPROM, conventional hard disks, CR-ROM, so-called flash memory, nonvolatile ROMS, RAM and a magnetic or optical storage medium. The medium may include instructions for causing a processor to perform any of the features described herein above for assessing the cardiac condition of a heart failure patient by measuring IVCT, patient activity and/or intrathoracic impedance, combining the measurements, storing same, and issuing notifications and alarms given certain combinations of same.

Various embodiments of the invention have been described. These and other embodiments including those having insubstantial changes from the foregoing are intended to be covered within the scope of the following claims.

The invention claimed is:

1. A method of assessing heart failure status in a patient, comprising:
   measuring a current inter-ventricular cardiac conduction time (IVCT);
   comparing the measured current IVCT to one of a programmable threshold IVCT and a previously measured IVCT; and
   responsive to the current IVCT differing from said one of the previously measured IVCT and the threshold IVCT, performing one of:
      storing the current IVCT in a memory structure,
      notifying a patient of a possible change in cardiac status,
      notifying a clinician of a possible change in cardiac status,
      generating an alarm,
   detecting myocardial ischemia, wherein detecting myocardial ischemia includes:
      comparing the detected conduction time to a threshold conduction time; and
      comparing a rate of change of the detected inter-ventricular cardiac conduction time to a range of change of inter-ventricular cardiac conduction times; and indicating a possible change in cardiac status when the detected inter-ventricular cardiac conduction time exceeds the threshold inter-ventricular cardiac conduction time and the rate of change of the detected inter-ventricular cardiac conduction time is within the rate of change.

2. A method apparatus according to claim 1, wherein generating an alarm comprises indicating that a heart failure hospitalization could be imminent.

3. A method according to claim 1, further comprising means for quantifying a degree of change in heart failure status based on the detected IVCT.

4. A method of assessing heart failure status in a patient, comprising:
   measuring a current inter-ventricular cardiac conduction time (IVCT);
   comparing the measured current IVCT to one of a programmable threshold IVCT and a previously measured IVCT; and
   responsive to the current IVCT differing from said one of the previously measured IVCT and the threshold IVCT, performing one of:
      storing the current IVCT in a memory structure,
      notifying a patient of a possible change in cardiac status,
      notifying a clinician of a possible change in cardiac status,
      generating an alarm; and
   prior to measuring a current inter-ventricular cardiac conduction time (IVCT), ascertaining whether an ischemic condition exists and if so then delaying measuring the current inter-ventricular cardiac conduction time (IVCT) for a period of time.

5. A method according to claim 4, wherein the step of determining whether an ischemic condition exists comprises determining whether an S-T segment deviation condition exists between at least two recent cardiac cycles.

6. A method apparatus according to claim 4, wherein generating an alarm comprises indicating that a heart failure hospitalization could be imminent.

7. A method according to claim 4, further comprising means for quantifying a degree of change in heart failure status based on the detected IVCT.

8. A method of assessing heart failure status in a patient, comprising:
   measuring a current inter-ventricular cardiac conduction time (IVCT);
   comparing the measured current IVCT to one of a programmable threshold IVCT and a previously measured IVCT; and
   responsive to the current IVCT differing from said one of the previously measured IVCT and the threshold IVCT, performing one of:
      storing the current IVCT in a memory structure,
      notifying a patient of a possible change in cardiac status,
      notifying a clinician of a possible change in cardiac status,
      generating an alarm; and,
   responsive to the previously measured IVCT and the currently measured IVCT differing by more than 20% then issuing a notification declaring one of a possible dislodgement of a medical electrical lead used to measure the IVCT and a possible migration of said medical electrical lead.

9. A method according to claim 8, further comprising:
   clearing the previously measured IVCT from memory; and
   resuming the method wherein the current IVCT is saved as the previously measured IVCT.

10. A method according to claim 9, wherein notifying the clinician comprises notifying the clinician that recalibration of the threshold may be required.

11. A method according to claim 8, wherein generating an alarm comprises indicating that a heart failure hospitalization could be imminent.

12. A method according to claim 8, further comprising quantifying a degree of change in heart failure status based on the detected IVCT.

13. A method of assessing heart failure status in a patient, comprising:
   measuring a current inter-ventricular cardiac conduction time (IVCT);
   comparing the measured current IVCT to a programmable threshold IVCT and a previously measured IVCT; and
   in the event that the current IVCT differs from said one of the previously measured IVCT and the threshold IVCT, performing one of:
      storing the current IVCT in a memory structure,
      notifying a patient of a possible change in cardiac status,
      notifying a clinician of a possible change in cardiac status,
      generating an alarm,
   wherein responsive to both the previously measured IVCT and the threshold IVCT being substantially greater than the current IVCT the notification to the patient and the clinician of a possible change in cardiac status includes a message that the cardiac status appears to have improved.

14. An apparatus for assessing heart failure status in a patient, comprising:
   means for measuring a current inter-ventricular cardiac conduction time (IVCT);
   means for comparing the measured current IVCT to one of a programmable threshold IVCT and a previously measured IVCT; and
   at least one of:
      means for storing the current IVCT in a memory structure,
      means for notifying a patient of a possible change in cardiac status, means for notifying a clinician of a possible change in cardiac status, means for generating an alarm; and means responsive to the previously measured IVCT and the currently measured IVCT differing by more than a predetermined amount for issuing a notification declaring one of a possible dislodgement of a medical electrical lead used to measure the IVCT and a possible migration of said medical electrical lead.

15. An apparatus according to claim 14, further comprising:

means for clearing the previously measured IVCT from memory; and means for resuming the method wherein the current IVCT is saved as the previously measured IVCT.

16. An apparatus according to claim 15, wherein notifying the clinician comprises notifying the clinician that recalibration of the threshold may be required.

17. An apparatus according to claim 14, wherein generating an alarm comprises indicating that a heart failure hospitalization could be imminent.

18. An apparatus according to claim 14, further comprising means for quantifying a degree of change in heart failure status based on the detected IVCT.

* * * * *